United States Patent
Mermelstein et al.

(10) Patent No.: US 7,273,889 B2
(45) Date of Patent: Sep. 25, 2007

(54) NMDA RECEPTOR ANTAGONIST FORMULATION WITH REDUCED NEUROTOXICITY

(75) Inventors: Fred H. Mermelstein, Upper Montclair, NJ (US); Randi Albin, North Bergen, NJ (US)

(73) Assignee: Innovative Drug Delivery Systems, Inc., New York, NY (US)

( * ) Notice: Subject to any disclaimer, the term of this patent is extended or adjusted under 35 U.S.C. 154(b) by 250 days.

(21) Appl. No.: 10/256,283

(22) Filed: Sep. 25, 2002

(65) Prior Publication Data
US 2004/0059003 A1   Mar. 25, 2004

(51) Int. Cl.
*A61K 31/137* (2006.01)
(52) U.S. Cl. .................. 514/650; 514/657; 514/665
(58) Field of Classification Search .............. 514/650, 514/657, 665; 424/423
See application file for complete search history.

(56) References Cited

U.S. PATENT DOCUMENTS

| | | | |
|---|---|---|---|
| 3,760,077 A * | 9/1973 | Thompson et al. ......... 514/326 |
| 4,017,619 A | 4/1977 | Burnap |
| 5,352,683 A | 10/1994 | Mayer |
| 5,384,331 A * | 1/1995 | Kogan et al. ............... 514/646 |
| 5,543,434 A | 8/1996 | Weg |
| 5,654,281 A | 8/1997 | Mayer |
| 5,834,465 A | 11/1998 | Olney |
| 5,919,826 A * | 7/1999 | Caruso ....................... 514/629 |
| 6,200,990 B1 | 3/2001 | Namil et al. |
| 6,248,789 B1 | 6/2001 | Weg |
| 6,509,028 B2 * | 1/2003 | Williams et al. ............ 424/434 |
| 6,638,981 B2 * | 10/2003 | Williams et al. ............ 514/656 |

FOREIGN PATENT DOCUMENTS

| | | |
|---|---|---|
| GB | 1330878 A1 | 9/1973 |
| WO | WO9851282 A2 * | 11/1998 |
| WO | WO-00/24396 A1 | 5/2000 |

OTHER PUBLICATIONS

"Creative Developments (Cosmetics) Limited: Surfactants 1999", www.creative-developments.co.uk, 1999.*
"Benzalkonium Chloride", www.en.wilipedia.org., 2006.*
R. Schmid et al.: "Use and efficacy of low-dose ketamine in the management of acute postoperative pain: a review of current techniques and outcomes," Pain, Amsterdam, vol. 82, No. 2, 1999, pp. 111-125.
Ahuja, Br. J. Anaesth. 1983, 55:991.
Battacharya et al., Ann. Acad. Med. Singapore 1994, 23:456.
Bookwalter, Plastic Surg. Nursing 1994, 14:43.
Brock-Utne et al., S.A. Med. J. 1982, 20:440.
Clark and Kalan, J. Pain Symptom. Manage. 1995, 10:310.
Collingridge et al., The NMDA Receptor, Oxford University Press, 1994.
Dich-Nielsen et al., Acta Anaesthesiol. Scand. 1992, 36:583.
Eide et al. Pain 1994, 58:347.
Errando et al. Reg. Anesth and Pain Med.1999, 24:136.
Fine,, J. Pain Symptom Manage. 1999, 17:296.
Fix et al, Experimental Neurology 1993, 123:204-215.
Fix et al., Toxicol. Pathol. 1996, 24:291-304.
Physicians' Desk Reference, 1986 Edition, Product Information, Cover page and pp. 1356-1358.
Mary Ellen Clinton et al., "Effects of Phenytoin, Ketamine, and Atropine Methyl Nitrate in Preventing Neuromuscular Toxicity of Acetylcholinesterase Inhibitors Soman and Diiospropylphosphorofluoridate", Journal of Toxicology and Environmental Health, 1988, Cover pages and pp. 439-449.
J.W. Olney et al., "NMDA Antagonist Neurotoxicity: Mechanism and Prevention", Science, vol. 254, Dec. 6, 1991, pp. 1515-1518.
Foster et al., Nature 1987, 329:395-396.
Gebhardt, Anaesthesist 1994, 43 (suppl.2):S34.
Gurnani et al., Anaesth. Intens. Care 1996, 24:32.
Hirlinger and Pfenninger, Anaesthsist 1987, 36:140.
Humphries e al., J. Burn Care Rehabil. 1997, 18:34.
Jevotovic-Todorovic et al., Brain Res 2001, 895;264.
Karpinski et al., Pain 1997, 73:103.
Kuboyama et al., J. Toxicol. Sci. 1997, 22:153.
Lauretti et al., Anesthesiology 1999, 90:1528.
Malinovsky et al., Anesthesiology 1991, 75:91.
Malinovsky et al., Anesthesiology 1993, 78:109.
Mathisen et al., Pain 1995, 61:215.
Mayer et al., Trends in Pharmacol. Sci. 1990, 11:254-260.
Mercadante et al., J. Pain Symptom Manage. 1995, 10:564.
Naguib et al., Can. Anaesth. Soc. J. 1986, 33:16.
Olney et al., Science 1989, 244:1360.
Shahar et al., Neurochem. Res. 1989, 14:1017.
Wlaz et al., Eur. J. Neurosci. 1994; 6:1710-1719.
Knox et al., Anaesth Intens Care 1995, 23:620-622.
Christophe Baudouin et al., Short term comparative study of topical 2% carteolol with and without benzalkonium chloride in healthy volunteers, British Jounal of Ophthalmology, vol. 82, pp. 39-42 (1998).
Neal L. Burstein, Preservative cytotoxic threshold for benzalkonium chloride and chlorhexidine digluconate in cat and rabbit corneas, Investigative Ophthalmology and Visual Science, vol. 19, pp. 308-313 (1980).

* cited by examiner

*Primary Examiner*—Brian Kwon
(74) *Attorney, Agent, or Firm*—Baker Botts L.L.P.

(57) ABSTRACT

The present invention is directed to pharmaceutical compositions of effective amounts of NMDA receptor antagonists and preservative for the administration to a patient in need of effective analgesia and anesthesia. The compositions of the invention advantageously do not cause any significant neurotoxicity. The preferred NMDA receptor antagonist is ketamine. The preferred preservative is benzalkonium chloride.

4 Claims, No Drawings

NMDA RECEPTOR ANTAGONIST FORMULATION WITH REDUCED NEUROTOXICITY

FIELD OF THE INVENTION

The present invention is directed to reducing toxicity of an NMDA receptor antagonist formulation. In particular, the invention is directed to an NMDA receptor antagonist composition which is administered for its analgesic and anesthetic effects, and which avoids significant neurotoxic side effects.

BACKGROUND OF THE INVENTION

An NMDA receptor is a postsynaptic, ionotropic receptor that is responsive to, inter alia, the excitatory amino acids glutamate and glycine and the synthetic compound NMDA. The NMDA receptor controls the flow of both divalent and monovalent ions into the postsynaptic neural cell through a receptor associated channel (Foster et al., Nature 1987, 329:395-396; Mayer et al., Trends in Pharmacol. Sci. 1990, 11:254-260). Activation of the NMDA receptor has been shown to be the central event which leads to excitotoxicity and neuronal death in many disease states, as well as a result of hypoxia and ischemia following head trauma, stroke and following cardiac arrest. The NMDA receptor has been implicated during development in specifying neuronal architecture and synaptic connectivity, and may be involved in experience-dependent synaptic modifications. In addition, NMDA receptors are also thought to be involved in long term potentiation and central nervous system disorders.

It is known in the art that the NMDA receptor plays a major role in the synaptic plasticity that underlies many higher cognitive functions, such as memory acquisition, retention and learning, as well as in certain nociceptive pathways and in the perception of pain (Collingridge et al., The NMDA Receptor, Oxford University Press, 1994). In addition, certain properties of NMDA receptors suggest that they may be involved in the information-processing in the brain that underlies consciousness itself.

NMDA receptor antagonists are therapeutically valuable for a number of reasons. In addition to anesthesia, certain NMDA receptor antagonists confer profound analgesia, a highly desirable component of general anesthesia and sedation. Also, NMDA receptor antagonists are neuroprotective under many clinically relevant circumstances (including neuropathic pain states, ischemia, brain trauma, and certain types of convulsions).

However, it is clear from the prior art that there are a number of drawbacks associated with current NMDA receptor antagonists. These include the production of involuntary movements, stimulation of the sympathetic nervous system, induction of neurotoxicity at high doses (which is pertinent since NMDA receptor antagonists have low potencies as general anesthetics), depression of the myocardium, and proconvulsions in some epileptogenic paradigms, e.g., "kindling" (Wlaz et al., Eur. J. Neurosci. 1994; 6:1710-1719). There have been considerable difficulties in developing new NMDA receptor antagonists that are able to cross the blood-brain barrier, which results in higher effective dosage requirements.

Commercially available NMDA antagonists have a wide variety of uses. For example, memantine provides rapid and enduring improvement in cognitive, psychological, social and motor impairments of dementia; dextromethorphan is used to relieve coughs; amantadine is an antiviral substance; and ketamine as an anesthetic agent. Certain opioids such as methadone, dextropropoxyphene, and ketobemidone are also classified as NMDA antagonists. MK-801 (dizocilpine maleate) and phencyclidine are not commercially used, and dextrophan, which is used commercially are other examples. However, a level of toxicity which accompanies these antagonists has proven to be problematic.

There are numerous potential commercial applications for NMDA antagonist formulations without neurotoxicity in supervised medical practice. Indications include, but are not limited to, treatment of dementia, suppression of cough (antitussive), antiviral treatment, treatment of involuntary muscle actions, antidepressant, suppression of addiction, and treatment of withdrawal. Ketamine, for example, can be used as an analgesic for breakthrough pain, anesthesia and sedation. Additional indications for ketamine include traumatic orthopedic injury pain, migraine pain, obstetrical use for end-stage labor pain, central pain, dental pain, and a host of additional conditions associated with acute and chronic, moderate to severe pain.

More specifically, ketamine, an NMDA receptor antagonist, has been in clinical use for over twenty-five years as a dissociative anesthetic and has demonstrated a wide margin of safety when used acutely as an anesthetic agent. Studies demonstrate the analgesic efficacy of ketamine in a variety of diverse indications including patient self-management of pain (U.S. Pat. Nos. 6,248,789 and No. 5,543,434 to Weg), post-operative analgesia (Naguib et al., Can. Anaesth. Soc. J. 1986, 33:16; Dich-Nielsen et al., Acta Anaesthesiol. Scand. 1992, 36:583; Battacharya et al., Ann. Acad. Med. Singapore 1994, 23:456), analgesia in emergency settings for patients suffering from fractures and soft tissue injury (Hirlinger and Pfenninger, Anaesthsist 1987, 36:140), musculoskeletal trauma (Gurnani et al., Anaesth. Intens. Care 1996, 24:32), wound care procedures (Bookwalter, Plastic Surg. Nursing 1994, 14:43; Humphries et al., J. Burn Care Rehabil. 1997, 18:34), management of acute episodes of neuropathic pain attributed to post-herpetic neuralgia (Eide et al., Pain 1994, 58:347), phantom limb pain (Knox et al., Anaesth. Intens. Care 1995, 23:620), nociceptive orofacial pain (Mathisen et al., Pain 1995, 61:215), and cancer pain (Mercadante et al., J. Pain Symptom Manage. 1995, 10:564; Clark and Kalan, J. Pain Symptom. Manage. 1995, 10:310; Fine, J. Pain Symptom Manage. 1999, 17:296; Lauretti et al., Anesthesiology 1999, 90:1528). These studies describe the use of ketamine administered by a variety of routes including transnasal, parenteral, and oral.

There are conflicting results from studies evaluating the potential for ketamine to cause neurotoxicity. Early in vitro studies examining the morphologic changes in cultured cells incubated with ketamine demonstrated that the drug induced, to a varied extent, damage of the myelin sheath and degeneration of mitochondria into multilamellar bodies in organotypic spinal cord slices derived from fetal rats (Shahar et al., Neurochem. Res. 1989, 14:1017). These apparent cytotoxic effects of ketamine were both dose-related and reversible. While no neurotoxic effects of ketamine have been observed in primates or rabbits, spinal cord lesions have been reported in rats and monkeys (Ahuja, Br. J. Anaesth. 1983, 55:991; Malinovsky et al., Anesthesiology 1991, 75:91; Gebhardt, Anaesthesist 1994, 43(suppl.2): S34). In addition, there is evidence of post-mortem histopathologic changes of subpial spinal cord vacuolation in a terminally ill cancer patient who received a continuous infusion of intrathecal ketamine at a rate of 5 mg/day for a duration of three weeks (Karpinski et al., Pain 1997, 73:103). Based on this finding, it was concluded that intrathecal ketamine may cause vacuolar myelopathy and that local vacuolation may be related to the lipophilicity of the drug. In addition, other studies have found that NMDA receptor antagonists, as phencycladine, MK-801, tiletamine, and ketamine cause neuronal vacuolization (Olney et al., Science 1989, 244:1360).

The studies describing the potential neurotoxic effects of ketamine are largely confined to administration of the drug by the intrathecal, or subarachnoid, route. Intrathecal administration of drugs may produce toxic reactions such as demyelination, arrachnoditis, and vascular changes and necrosis.

According to standard practice, ketamine is usually employed containing a preservative. Studies comparing the neurotoxicologic profile of preservative-free ketamine to ketamine containing preservative (chlorobutanol or benzethonium chloride) yielded curious results. Experiments with baboons, monkeys, rabbits, and rats receiving between 0.2 and 50 mg intrathecal ketamine with and without preservative failed to demonstrate histopathologic central nervous system lesions attributable to the drug, but nonetheless detected a breach of the blood brain barrier that was attributable to the presence of preservative (Malinovsky et al., Anesthesiology 1993, 78:109; Karpinski et al., Pain 1997, 73:103). The results were surprising since the combination of a drug with a preservative may also cause, or exacerbate, neurological damage due to the preservative itself (Brock-Utne et al., S.A. Med. J. 1982, 20:440). A further comparative study of multiple dose intrathecally administered preservative-free ketamine, ketamine containing the preservative benzethonium chloride, and benzethonium chloride alone was performed in an attempt to resolve the apparent discrepancies in the animal models (Errando et al., Reg. Anesth and Pain Med. 1999, 24:146). The results of this analysis demonstrated that preservative-free ketamine was without neurotoxic effect. However, ketamine with preservative produced minor changes to the spinal cord of the animals, and benzethonium chloride alone produced moderate neurotoxic effects (Errando et al., Reg. Anesth and Pain Med. 1999, 24:146). The results of this study confirm the lack of apparent independent neurotoxicity of ketamine and support the view that preservative-free ketamine is safe for intrathecal use in humans, even for repeated injections.

This observation was of limited value, however, since, while single-dose preparations may not require preservatives, other substances require the addition of preservatives to prevent or inhibit microbial growth and avoid spoilage of the preparation. Benzethonium chloride, a quaternary ammonium salt, is a common preservative similar to other cationic surfactants. The animal models, noted previously, indicated that the accompanying preservative, benzethonium chloride, and not ketamine itself, is the likely culprit mediating neurotoxicity in the anesthetic formulation following intrathecal administration of the drugs. With the known neurotoxic effects of this class of preservative, there remains a need in the art for a safe and effective analgesic and anesthetic formulation. The present invention addresses this need with a unique formulation which inhibits or diminishes the neurotoxicity.

SUMMARY OF THE INVENTION

It has now been discovered that benzalkonium quaternary ammonium compounds can be effectively used as preservatives for NMDA receptor antagonists which achieve the desired analgesic and anesthetic effects, without neurotoxic side effects. This discovery runs contrary to evidence of neurotoxicity associated with the administration of NMDA receptor antagonists or antagonists with preservative. Thus, the invention provides greater safety of prepared NMDA receptor antagonist formulations, which avoids the need to prepare preservative-free solutions before every use.

The invention addresses the need in the art for effective preservatives which have no observable propensity to cause neurotoxicity, such as neuron vacuolation or degeneration. The discovery is particularly surprising in that the benzalkonium compound is of the same class of compounds as the benzethonium compound which, as described above, has demonstrated neurotoxic side effects. Both are benzyl quaternary compounds, which are cationic surfactants.

A particularly preferred NMDA receptor antagonist for use in the invention is ketamine. A preferred benzalkonium compound is benzalkonium chloride.

DETAILED DESCRIPTION

The present invention provides a formulation comprising a preservative selected from the benzalkonium chloride quaternary ammonium salts, and a therapeutically effective dose of an NMDA receptor antagonist, i.e., a dose effective to alleviate pain. The invention avoids the neurotoxicity of other preservatives and provides a formulation with reduced or close to no neurotoxicity. The composition is administered for the analgesic or anesthetic effects without causing any significant neurotoxic side effects.

The use of intranasal ketamine has been studied as a safe and effective treatment for patients suffering from breakthrough pain. Because breakthrough pain can occur in chronic pain conditions, such as cancer, consideration was given to the possibility of neurotoxicity of transnasal ketamine compositions containing benzethonium chloride. The present invention is based on the discovery that ketamine formulations, as studied in rats, containing benzalkonium chloride as a preservative demonstrated no observable effects in neuron vacuolation or degeneration.

The present invention addresses the need in the art for pharmaceutical compositions comprising an NMDA receptor antagonist with an effective preservative having reduced neurotoxicity. Benzalkonium chloride is used at relatively low concentrations (0.001-0.02%) and has optimal activity when pH is greater than 4, and at a pH up to 10, is stable at room temperature. Benzalkonium chloride is widely used as a preservative in commercial nasal sprays. Nasal irritation has been associated with chronic use of certain nasal products, and there have been isolated reports of the ability of benzalkonium chloride to cause irritation to the nasal mucosa. However, there appears to be no effect at the concentration intended for use in the present invention's formulation (Kuboyama et al., J. Toxicol. Sci.1997, 22:153).

The NMDA receptor antagonists used in the invention include, but are not limited to ketamine, dextromethorphane, dextrophan, methadone, dextropropoxyphene, ketobemidone, and phencycladine. In the preferred embodiment, the NMDA receptor antagonist is ketamine.

Other examples of antagonists include competitive and non-competitive antagonists. The competitive NMDA antagonists include 2-amino-7-phosphonoheptanoic acid (AP 7) and analogs; 3-(($\pm$)2-carboxy-piperazin-4-yl)-propyl-1-phosphonic acid (CPP) and analogs; (e)-4-(3-phosphonoprop-2-enyl)piperazine-2-carboxylic acid (CPPenes) and analogs; cis-4-phosphonomethyl-2-piperidinecarboxylic acid (CGS 19755); DL-(E)-2-amino-4-methyl-5-phosphono-3-pentanoic acid (CGP 40115) enantiomers and analogs; S-$\alpha$-amino-5-phosphonomethyl-

[1,1'-biphenyl]-3-propanoic acid, E-2-amino-4-methyl-5-phosphono-3-pentenoic acid, E-2-amino-4-methyl-5-phosphono-3-pentenoic acid ethyl ester, cis-4-phosphonomethyl-2-piperidinecarboxylic acid, (R)-4-oxo-2-amino-5-phosphono-pentanoic acid, 2-amino-4,5-(1,2-cyclohexyl)-7-phosphonoheptanoic acid, 4-(phosphonomethyl)-DL-phenylglycine, 4-(3-phosphono-propyl)-2-piperidinecarboxylic acid, 2-(2-phosphonoethyl)-DL-phenylalanine, 3-carboxy-5-(phosphonoethyl)-1,2,3,4-tetrahydroisoquinoline, 3-carboxy-5-phosphono -1,2,3,4-tetrahydroisoquinoline, cis-DL-4-[(1(2)H-tetrazol-5-yl)methyl]2-piperidinecarboxylic acid, cis-4-(3-phosphonoprop-1-enyl)-2-piperidinecarboxylic acid, E-2-amino-4-propyl-5-phosphono-3-pentenoic acid, phosphoric acid-4-(2-carboxy-piperidinyl) ester, and 1-[4(4-chloro-α,α-dimethylbenzyl)-2-methoxyphenyl]-1,2,4-triazole-3-carboxylic acid amide. Noncompetitive NMDA antagonists include memantines and other amantadine analogs; budipine and analogs; ifenprodil and analogs; antagonists of the glycine binding site kynurenic acid and analogs; 1-hydroxy-3-aminopyrrolidin-2-one (HA-966) and analogs; polyamines such as spermine and spermidine and analogs: inhibitors of the excitatory amino acid synthesis.

When used as an anesthetic, i.e., to substantially eliminate all sensation, the dosage range is broadly from 1 mg/kg to 15 mg/kg, and preferably from 1 to 4.5 mg/kg over a period of about 1 minute delivered I.V. and 6.5 to 13 mg/kg via intramuscular injection.

On the other hand, when ketamine is used as an analgesic, i.e., to reduce or eliminate pain, the dosage range is broadly from 0.01 mg/kg to 1 mg/kg, and preferably from 0.05 mg/kg to 0.7 mg/kg.

The preservatives used in the invention are benzalkonium chloride quaternary ammonium salts. These compounds have the formula:

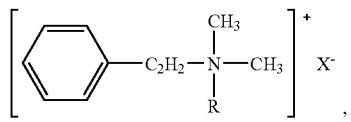

wherein X is a halide. The phenyl ring may also have a Cl substitution. The R is an alkyl group having from 10 to 22 carbon atoms, preferably 12 to 16 carbon atoms. The X may be bromide or iodide, but is preferably chloride. Most preferably R is a mixture containing $C_{12}$ and $C_{14}$ alkyl groups, and X is most preferably chloride, otherwise known as benzalkonium chloride.

The amount of the preservative administered ranges from about 0.001% to about 0.2% per unit dose, preferably from about 0.07% to about 0.14% per unit dose.

Other agents may be used in the invention, for example those that can be used for delivery including liposomes, microparticles (including microspheres and microcapsules) and other release devices and forms that provide controlled, prolonged or pulsed, delivery or which enhance passage through the blood brain barrier. Suitable pharmaceutical carriers, known to those skilled in the art, may also be used. These are described in *Remington's Pharmaceutical Sciences*, 17th ed., Mack Publishing Co., Easton, Pa., p.1418 (1985), a standard reference text in this field, incorporated herein by reference. Antioxidizing agents such as sodium bisulfite, sodium sulfite, or ascorbic acid either alone or combined are suitable stabilizing agents. Also used are citric acid and its salts and sodium EDTA.

Administration of the NMDA receptor antagonist can be by way of oral, transmucosal (buccal, nasal and rectal), transdermal, intramuscular, or intraocular route, or by parenteral administration. The parenteral routes of administration include, but are not limited to, intravenous, intramuscular, intrathecal, epidural, intracerebroventricular, intradermal/intracutaneous, or subcutaneous injections. Other parenteral routes may include intraarticular (into the joints), intrasynovial (a joint-fluid area), intraspinal, intraarterial, and intracardiac. Any two or more routes of administration can be combined, such as intravenous and transdermal.

As those skilled in the art recognize, many factors that modify the action of the active substance herein will be taken into account by the treating physician such as the age, body weight, sex, diet and condition of the patient, the time of administration, the rate and route of administration, and so forth. Optimal dosages for a given set of conditions can be ascertained by those skilled in the art using conventional dosage determination tests in view of the experimental data provided herein.

The present invention is intended for use in animals. In a preferred embodiment, the invention is used with mammals. In another embodiment, the invention is directed to use in humans. The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

As used herein, the term "antagonist" refers to a compound that renders the active agent unavailable to produce a pharmacological effect. In other words, the antagonist, itself, does not produce a particular pharmacological effect, but rather blocks the ability of an active agent to produce that effect. In a specific embodiment, the antagonist interacts with the same receptor as the active agent and inhibits the interaction of the active agent with the receptor. The term "antagonist" as used herein includes any compound that reduces the flow of cations through an ionotropic receptor such as NMDA, i.e., a channel closer, and which has not been observed to increase the flow of cations through the same receptor.

A "therapeutically effective amount" of a drug is an amount effective to demonstrate a desired activity of the drug. According to the instant invention, in one embodiment a therapeutically effective amount of ketamine is an amount effective to alleviate, i.e., noticeably reduce, pain in a patient. In another embodiment, a therapeutically effective amount is an amount effective to enhance another pain therapy, e.g., a pain medication such as a narcotic. In still another embodiment, it is an amount effective to induce anesthesia.

The term "neurotoxicity" as used herein refers to the level of neuron degeneration or necrosis, e.g., as measured by neuronal vacuolation or behavioral changes after exposure to the NMDA antagonist composition. The NMDA receptor antagonist formulation of the present invention is one in which the neurotoxicity of the composition is reduced or close to none. The term "close to none" means a level of neurotoxicity, if any, that cannot be detected by a particular assay method.

The term "nontoxic" as used herein shall be understood in a relative sense and is intended to designate any substance that has been approved by the United States Food and Drug Administration ("FDA") for administration to humans or, in keeping with established criteria, is susceptible to approval by the FDA for administration to humans. The term "non-toxic" is also used herein to describe the NMDA receptor antagonists, or blockers, that are useful in the practice of the present invention from NMDA receptor antagonists such as MK-801 whose toxicities effectively preclude their therapeutic use.

As used herein, the term "pharmaceutically acceptable" refers to a biologically or pharmacologically compatible for in vivo use, and preferably means approved by a regulatory agency of the Federal or a state government or listed in the U.S. Pharmacopeia or other generally recognized pharmacopeia for use in animals, and more particularly in humans.

The following Example(s) illustrate the invention, but are not limiting.

EXAMPLE 1

Randomized, Placebo-Controlled, Double Blind Study of the Safety and Efficacy of PMI-100 for the Treatment of Breakthrough Pain in Patients with Chronic Malignant Pain This example evaluates the safety and efficacy of a ketamine hydrochloride formulation with preservative delivered through a nasal spray. Plasma levels were measured for the bioavailability and for correlating blood levels with analgesic effect.

Methods

The study is a randomized, multi-center, placebo-controlled, double-blind, crossover trial with 20 patients who had chronic malignant pain and a pattern of 2-7 episodes of daily breakthrough pain, despite taking stable doses of analgesic medication. After an initial screening visit (visit 1), patients completed 2 study visits at least 48 hours apart; one visit for treatment with a PMI-100 formulation (visit 2), and a second visit for treatment with placebo (visit 3). The PMI-100 formulation is an aqueous intranasal ketamine formulation containing 10% (w/v) ketamine hydrochloride solution and 0.002% benzalkonium chloride solution. The placebo control is an aqueous solution of 0.002% benzalkonium chloride solution alone.

When pain intensity at the onset of breakthrough pain episodes were greater than or equal to 5 on the Numeric Pain Intensity Scale (NPIS), patients self-administered 1-5 sprays (90 seconds apart, alternating nostrils) of the PMI-100. If the episode was less than 5, the patients were advised to wait for another episode. Treatment duration varied depending on the number of sprays of study medication administered by the patient.

The primary efficacy parameter was the difference between the average of the 9 post-treatment NPIS measurements and the baseline pre-treatment NPIS pain measurement. Secondary efficacy parameters included: NPIS pain measurements at each of 10 time points, the Investigator's opinion of the treatment response (rated as "good," "fair," or "poor"), and the proportion of subjects with at least a 40% reduction of the NPIS measurement from baseline to the end of treatment; where "end of treatment" was defined as the average of the 9 post-baseline NPIS scores. Another parameter of interest was the proportion of subjects who took rescue medication during the breakthrough pain episode.

Safety assessments consisted of monitoring and recording all adverse and serious adverse events, measurement of hematology and blood chemistry parameters, measurement of vital signs, measurement of nasal symptoms, including an assessment of the side effects utilizing a rating scale for dissociative anesthetics. The primary safety parameter was the results from the Side Effects Rating Scale for Dissociative Anesthetics. The scale was administered immediately after the final NPIS rating was done (approximately 60 minutes after the first administration of study medication) and then again 24 hours after administration of the study drug.

Patients were asked to rate any of the side effects included in the scale that may have occurred since using the study medication. Side effects that were rated included: fatigue, dizziness, nausea, headache, feeling of unreality, changes in hearing, changes in vision, mood change, generalized discomfort and hallucination. The degree of severity of each of these side effects was rated as: 0=No change; 1=weak; 2=modest; 3=bothersome; 4=very bothersome. Other adverse events were recorded separately. The Investigator recorded on the CRF whether each adverse event was best described as UNRELATED, POSSIBLY RELATED, PROBABLY RELATED, DEFINITELY RELATED or of UNKNOWN association to the study medications.

Hematology [hemoglobin, hematocrit, PT, PTT, red blood cells (RBC), white blood cells (WBC) with differential and platelet count], blood chemistry [sodium, $CO_2$, potassium, calcium, phosphorous, chloride, glucose, blood urea nitrogen, serum creatinine, serum uric acid, total serum protein, serum albumin, total bilirubin, lactate dehydrogenase (LDH), liver function tests (AST, ALT, alkaline phosphatase)], were measured prior to the treatment and after the treatment at both Visits 2 and 3.

Plasma levels of ketamine and its metabolites were measured at baseline, and at 2 minutes, 30 minutes, and 60 minutes following the last spray of study medication for each patient.

Vital signs (body temperature, systolic blood pressure, diastolic blood pressure, pulse oximetry and heart rate) were measured at Visit 1 (screening), and pre-treatment, during treatment (at 10, 20, 40 and 60 minutes) and post-treatment at Visits 2 and 3.

Nasal symptoms included the incidence of nasal pain, nasal congestion, sinus pain, sinus headaches, nosebleeds, change in smell, change in taste, runny nose, bad odor in nose, dry nose, postnasal drip, excess tearing and headaches.

The severity of break through pain episodes was rated using a Numeric Pain Intensity Scale (NPIS). The NPIS is a commonly used tool for the assessment of pain. The Side Effects Rating Scale for Dissociative Anesthetics provides an assessment of experiences likely to be induced by near-anesthetic doses of drugs such as ketamine. The use of ketamine hydrochloride as an anesthetic agent has resulted in the occurrence of postoperative confusional states known as "emergence reactions" in approximately 12 percent of patients. The psychological manifestations have varied in severity, and in some cases have been accompanied by confusion, excitement, and irrational behavior recalled by a few patients as an unpleasant experience. The duration ordinarily was no more than a few hours; in a few cases, however, recurrences took place up to 24 hours postoperatively. Thus the Side Effects Rating Scale for Dissociative Anesthetics was administered immediately after treatment (approximately 60 minutes after the first dose of study medication) as well as 24 hours after treatment with study medication.

Efficacy.

The primary efficacy analysis consisted of a two-stage crossover analysis of a summary measure of change in NPIS pain measurement. The summary measure of change in NPIS pain measurement was calculated by averaging the 9 post-treatment NPIS pain measurements, and then subtracting the baseline NPIS pain measurement. The tests for a differential carryover effect and period effect were performed using Wilcoxon rank sum statistics with exact critical values. If no carryover or period effects were noted, treatment effect was assessed by comparing within patient differences using the Wilcoxon signed rank test. If a significant carryover effect was detected, treatment effect was assessed using Visit 2 data only, with the Wilcoxon rank sum test. The Wilcoxon signed rank statistic and the Wilcoxon rank sum tests were obtained using exact critical values.

As a secondary analysis, if there was no evidence of a carry-over effect in the primary analysis, a Friedman's Repeated Measures Analysis of Variance on Ranks test was used to compare the NPIS responses at the 10 time points within each treatment group. If there was a statistically significant carry-over effect (p<0.10) in the primary analysis, then the Friedman's test was calculated on Visit 2 data only. Secondary analyses also included the proportion of subjects who exhibited at least a 40% reduction in NPIS from baseline to the end of treatment (where "end of treatment" was defined as the average of the 9 post baseline NPIS scores), with PMI-100 vs placebo. These proportions were compared using the exact version of McNemar's test for matched proportions.

The investigator's opinion of response to therapy under each treatment regimen was summarized as a cross tabulation table. The exact version of the marginal homogeneity test was performed. Another parameter of interest was the proportion of evaluable subjects who chose to use rescue medication during the breakthrough pain episode under the placebo condition, versus the proportion who chose to use it under the active treatment condition. These figures were described by cross tabulations and compared by the exact version of McNemar's test for matched proportions.

Safety.

Cross tabulations of the responses by treatment were presented for the Side Effects Rating Scale for Dissociative Anesthetics evaluated post-evaluation and 24-hours post-evaluation. The exact version of the marginal homogeneity test was performed. The incidence of adverse events by treatment and by visit were displayed for all adverse events, serious adverse events and associated adverse events. For routine laboratory and chemistry parameters and vital signs, continuous outcomes were analyzed using the Wilcoxon Signed Rank test. In addition, summary statistics (sample size, mean, median, standard deviation, and range) were also presented for each treatment. The number and percent of patients experiencing specific nasal complaints under each treatment were tabulated.

Plasma levels of ketamine and its metabolites (norketamine and dehydronorketamine) were measured and listed for each patient at baseline, 2 minutes, 30 minutes, and 60 minutes following the last spray of study medication. 10 ml blood samples were drawn, and replaced with 10 ml saline. The blood samples were drawn into a heparinized tube, which was subsequently gently inverted 10 to 15 times, and centrifuged until cells and plasma were separated. At least 5 ml plasma were transferred into 7 ml storage vial, labeled, and frozen immediately at −20° C.

Results

Treatment of breakthrough pain with PMI-100 demonstrated significant reductions in pain intensity compared to treatment with placebo in this cross-over study. Mean reduction from the baseline NPIS pain score was 2.65 (mean summary measure of change over the 9 post-treatment observation time points) units in the PMI-100 treatment group compared to 0.81 units in the placebo treatment group (p<0.0001). Fifteen of 20 (75%) of patients administered the maximum 5 sprays of PMI-100. Statistically significant reductions in pain intensity compared to placebo occurred as early as the 10 minute observation period, or 4 minutes following administration of the 5 spray, and significance continued through the 60 minute observation time point. Nineteen of 20 patients (95%) reported reduction in pain intensity within the 60 minute observation period after treatment with PMI-100, while only 10 of these 20 patients (50%) reported a reduction after treatment with placebo. Nine patients (45%) had an average reduction in NPIS score of 40% or greater following treatment with PMI-100 compared to only one patient (5%) following treatment with placebo(p=0.0078). Zero out of 20 patients requested rescue medication during the 60-minute breakthrough pain episode observation period while 7 of 20 (35%) requested rescue medications after treatment with placebo (p=0.0156).

The investigator's global assessment of the patient's general condition following study medication was "good" for 16 of 20 (80%) patients, irrespective of whether the patient was being treated with PMI-100 or placebo. After PMI-100 treatment, 18 of 20 (90%) patients were assessed as "good", one patient was assessed as "fair" and only one patient was assessed as "poor". Four patients were assessed as "poor" during treatment with placebo.

After treatment with PMI-100, 13 of 20 (65%) patients achieved a minimum NPIS score that was at least 40% lower than the pre-treatment score, compared with only 4 of 20 (20%) in the placebo group. The clinical significance of this effect is further demonstrated by the observation that 14 of 20 (70%) patients treated with PMI-100 achieved a NPIS score of 4 or less, the target used by most pain guidelines, and 11 of 20 (55%) patients attained a minimum NPIS score of 2.2 or less while an equivalent reduction in NPIS score was achieved only in 2 of 20 (10%) patients after treatment with placebo. By contrast, after administering treatment with placebo, 10 of 20 (50%) patients reported no reduction in NPIS score during the 60 minute breakthrough pain episode while only 1 patient reported no relief after treatment with PMI-100.

Equally impressive from a clinical perspective, is the rapidity of pain relief, with 15 of 20 (75%) achieving their minimum NPIS score within 25 minutes, and 8 achieving their minimum NPIS score within 5-10 minutes following treatment with PMI-100. Statistically significant pain relief occurred within 4 minutes of the delivery of the final intranasal spray of PMI-100 (10 minutes from initial spray). See Table A below.

TABLE A

NPIS Score-Change from Baseline over Time-Modified Intent-to-Treat Population

| | Time after Start of Administration of Study Drug (Minutes)[a] | | | | | | | | |
|---|---|---|---|---|---|---|---|---|---|
| | 5 | 10 | 15 | 20 | 25 | 30 | 40 | 50 | 60 |
| PMI-100 | −1.50 | −2.45 | −2.79 | −2.51 | −3.03 | −2.98 | −3.13 | −2.86 | −2.47 |
| Placebo | −0.56 | −0.67 | −0.83 | −0.83 | −0.94 | −0.96 | −0.79 | −0.77 | −0.98 |
| P-value[b] | 0.2114 | 0.0039 | 0.0007 | 0.0010 | 0.0003 | 0.0007 | 0.0001 | 0.0001 | 0.0037 |

[a] Administration of PMI-100 may not have completed until 7.5 minutes after start of dosing
[b] Wilcoxon signed rank test comparing change between treatment groups A statistically significant between-treatment difference in the mean change of the NPIS score was observed as early as 10 minutes after initiation of treatment and persisted for remainder of the 60 minute observation period. For the 15 (75%) patients administering 5 sprays, statistically significant changes in NPIS score occurred as early as 4 minutes following the final spray. The greatest improvements in the NPIS score occurred in the PMI-100 treated group between 25 and 40 minutes after initiation of treatment. This corresponds with plasma levels of ketamine that were higher at the 30 minute post final spray observation point compared to the 2 minute and 60 minute post final spray observation points. Analyses were repeated for a per-protocol population. Analyses suggested evidence of a period effect (p=0.0350) although subjects who were administered PMI-100 still had an advantage over those administered placebo at both Visit 2 (3.46 units vs. 1.20 units, p=0.0734) and Visit 3 (2.05 units vs. 0.45 units). Results from the GEE analysis suggested that after adjusting for a period effect (p=0.0207), the reduction from baseline was on average 1.93 units greater following treatment with PMI-100 than placebo (p=0.0029).

Based on the NPIS score reported, a rank was assigned to each of the 10 visit time points for each patient. The maximum rank that could be assigned to a time point was 10. However, if a patient reported the same NPIS score at more than one time point, the average rank would be assigned to each of those equivalent time points. The median of the ranks of the 20 patients was then calculated at each time point. The median rank of the pre-treatment time point (time 0) was 9.5 for patients following PMI-100 treatment and the $25^{th}$-$75^{th}$ percentile range was 8.3 to 10.0. This would imply that the pain of maximum intensity was felt at time 0. Over time the median dropped and the range of the distribution shifted lower. At 60 minutes the median was 6.8 with a $25^{th}$-$75^{th}$ percentile range of 3.0 to 8.5. Friedman's test p-value of <0.0001 (0.0007 following treatment with placebo) suggests that there is a difference in the distribution of ranks over the 60 minutes, and the contrast p-value of <0.0001 (0.0386 following treatment with placebo) indicates that there is a difference between time 0 and the average of the post-treatment values.

Following the administration of study medication, the investigator evaluated the patient's general condition as good, fair or poor. Since the investigator's global assessment was "good" following either PMI-100 or placebo treatment for 16 of 20 (80%) patients, this assessment proved not to have discriminatory potential. This group included all 15 patients evaluated at Site 01. Three patients were assessed as "poor" following treatment with placebo and required rescue medication during the breakthrough pain episode. Of the 20 patients in the study, only patient 164 from Site 03, received an assessment of "poor" after treatment with PMI-100. Patients in the per-protocol population were assessed as "good" following treatment with both PMI-100 and placebo.

The number of patients that were able to attain a 40% reduction in NPIS score from the pre-treatment score to the mean of the 9 post-treatment observations was compared between treatment with PMI-100 and treatment with placebo. Nine of 20 (45%) patients attained a mean of the 9 post-treatment observations that represented at least a 40% reduction from their pre-treatment NPIS score following treatment with PMI-100. These were patients 106, 107, 110, 112, 115, and 117 from Site 01 and 162,163 and 165 from Site 03. Patient 110 from Site 01 also attained a 40% reduction following treatment with placebo. This treatment difference in ability to attain a greater than 40% reduction in NPIS score was shown to be statistically significant compared to placebo (p=0.0078) using McNemar's test for paired data.

Use of rescue medication during the 60-minute breakthrough pain evaluation period was compared between patients being treated with PMI-100 and those being treated with placebo. Zero of 20 patients required rescue medication during the breakthrough period when treated with PMI-100, compared to 7 of 20 patients that required rescue medication during the breakthrough period after treatment with placebo (p=0.0156).

Efficacy Conclusions.

The results of the study indicate that intranasal ketamine hydrochloride (PMI-100), administered at doses ranging from 10 mg to 50 mg, provides rapid, meaningful pain relief during intense breakthrough pain episodes that otherwise are poorly managed. Placebo control had no effect in alleviating pain. The onset of statistically significant reductions in pain intensity after treatment with PMI-100 was within 10 minutes of the first spray, and within 4 minutes for patients who administered the full 5 sprays. Furthermore, 75% of patients treated with PMI-100 achieved their minimum NPIS score within 25 minutes of administration. The magnitude of the average decrease in pain intensity compared to placebo was statistically significant over the 60 minute observation period, and a statistically significant number of patients averaged a >40% reduction in their NPIS scores. The time-specific significant reductions in pain intensity after treatment with PMI-100 started at 10 minutes and continued through the 60 minute observation point. The efficacy data presented here is clinically significant. Zero of 20 patients required use of rescue medications in the 60 minutes following administration of PMI-100, representing the potential for lower daily opioid use. Although patients were not required to administer 5 sprays, or 50 mg, of PMI-100 the majority (75%) did, indicating that the therapeutic dose is possibly towards the higher end of the range. Patients who delivered less than 5 sprays did indicate substantial reductions in pain intensity however, which supports a self-titrating approach might be necessary with this test product.

Safety Evaluation.

Using the Rating Scale for Dissociative Anesthetics, which was a retrospective questionnaire administered to each patient 60 minutes post-study drug administration, possible dissociative-type side effects were evaluated. The questionnaire was administered again 24 hours after study drug administration to evaluate any lingering effects of intranasal ketamine.

Overall there were few dissociative side effects reported, and the majority of effects were mild to moderate in severity and had resolved by the time the questionnaire had been administered 60 minutes after dosing. Nine of 20 (45%) patients reported some type of dissociative effect following treatment with PMI-100 compared to only 1 (5%) patient after treatment with placebo. The most commonly reported effects reported on the questionnaire after treatment with PMI-100 were fatigue (7 patients), dizziness (4 patients), feeling of unreality (4 patients), and changes in vision (2 patients). Of these commonly reported effects, less than 10% of the treatment group indicated that they were "bothersome" or "very bothersome" in nature. Only one patient (5%) indicated a "general feeling of discomfort" after treatment with PMI-100. With the exception of 2 patients with fatigue, and one patient with nausea, there were no side effects reported on the 24 hour post-drug administration dissociative side effects questionnaire. There were no reports of hallucinations following treatment with intranasal PMI-100, nor were any interventions with benzodiazipines required.

The majority of bothersome and very bothersome dissociative effects reported were experienced by three patients, all of whom administered the maximum 5 sprays of PMI-100: 1) Patient 165 experienced very bothersome dizziness and feeling of unreality post-evaluation. The patient also experienced dizziness and headache during placebo administration. This patient also had a fluctuation of blood pressure, with a pre-episode blood pressure of 142/86. Twenty minutes into the breakthrough pain episode, the patient's blood pressure rose to 169/88. At post-evaluation, the patient's blood pressure was 103/53. 2) Patient 117 experienced 7 side effects post-evaluation which included fatigue (bothersome), dizziness (bothersome), feeling of unreality (moderate), change in hearing (moderate), change in vision (mild), mood change (moderate), and generalized discomfort (bothersome). 3) Patient 105 experienced fatigue (bothersome), feeling of unreality (bothersome), and a change in vision (moderate) at post-evaluation. It should be noted that this patient had a medical history significant for blurry vision in the past, so this is possibly not related to the drug.

No patients, following administration of either PMI-100 or placebo, experienced dizziness 24 hours post evaluation. No patients, following administration of either PMI-100 or placebo, experienced headache post-evaluation, or 24 hours post-evaluation. No patients, following administration of either PMI-100 or placebo, experienced a feeling of unreality 24 hours post-evaluation. No patients, following administration of either PMI-100 or placebo, reported changes in hearing 24 hours post-evaluation. No patients, following administration of either PMI-100 or placebo, experienced changes in vision 24 hours post-evaluation. No patients, following administration of either PMI-100 or placebo, reported mood change 24 hours post-evaluation.

No patients, following administration of either PMI-100 or placebo, experienced generalized discomfort 24 hours post-valuation.

A pre- and post-treatment nasal symptom assessment was performed as part of the safety assessment of PMI-100 and placebo. The nasal spray, at a concentration of 100 mg/ml, and a dose of 10 to 50 mg (one to 5 sprays), was very well tolerated with few effects noted on the nasal symptom exam. A change in taste that was not present pre-treatment was reported for 3 patients (#162, 163 and 165 from Site 03) following treatment with PMI-100. Nasal congestion, sinus pain, runny nose and post-nasal drip were also reported nasal symptoms. These symptoms were all present pre-treatment and may or may not have been observed post-treatment.

A total of 10 patients experienced adverse events after treatment with either PMI-100 or placebo. All but 4 treatment-emergent adverse events were considered to be associated treatment emergent adverse events, those events deemed by the investigator as either possibly, probably, or definitely related to the study medication. Six of 20 (30%) patients that received PMI-100 experienced an associated treatment-emergent adverse event categorized under the body system of nervous system disorders. Two of 20 (10%) patients that received placebo reported adverse events that fell into this category.

Two of 20 (10%) patients experienced a moderate elevation in blood pressure within 15 minutes following administration of the full dose (50 mg) of PMI-100. Patient 164 had an initial pre-episode blood pressure of 165/69 prior to treatment with PMI-100. During this breakthrough pain episode, the patient's blood pressure rose to 212/88. Approximately 60-minutes after the first spray of PMI-100 the patient's blood pressure was 191/84. This adverse event fell under the body system "investigations" and had a preferred term of "blood pressure increased." This patient's blood pressure also rose during the breakthrough pain episode that was treated with placebo. The patient had a pre-episode blood pressure of 155/70. At 60-minutes, the patients' blood pressure had risen to 187/85, and then dropped back down to 154/73 at post-evaluation. Patient 165 also experienced an increase in blood pressure during the breakthrough pain episode that was treated with PMI-100. The patient's pre-episode blood pressure was 142/86. At 20-minutes, the patient's blood pressure had risen to 169/88. At post-episode evaluation, the patient's blood pressure had dropped to 103/53. This adverse event fell under the body system of "vascular disorders" and had a preferred term of "hypertension NOS."

Only 4 treatment-emergent adverse events were considered not associated to the study medication, 2 occurred following treatment with placebo (mild laceration, nausea) and 2 following treatment with PMI-100 (pyrexia, nasal congestion). No serious treatment emergent adverse events occurred during the study. One patient (165) from study Site 03 experienced a serious adverse event during the screening phase of the study. Patient 165 experienced intractable vomiting and was hospitalized due to this serious adverse event. This event was considered unrelated to the study medication, since the patient had not received any study medication at the time of the event.

Safety Conclusions.

Intranasal ketamine (PMI-100) was well tolerated with no serious adverse events, deaths, or treatment-related dropouts on study. The majority of adverse events were mild in severity and transient in nature, with "change in taste" or "taste disturbance" being the most frequently reported effect after treatment with PMI-100. During treatment with either PMI-100 or placebo, safety was assessed through the reporting of specific side effects using the Side Effects Rating Scale for Dissociative Anesthetics, the existence of nasal symptoms assessed during a nasal exam, the monitoring of adverse events and the measurement of vital signs, routine hematology and blood chemistry results.

The results from the retrospective solicitation of possible dissociative side-effects indicated that mild, transient fatigue, dizziness, and a feeling of unreality were the most commonly chosen items from the questionnaire. Both dizziness and feelings of unreality were reported by 4 out of the 20 subjects treated with PMI-100, while fatigue was reported by 9/20 patients after treatment with PMI-100. The majority of dissociative effects following treatment with PMI-100 were experienced by 3 patients. The twenty-four hour post study dissociative side effect questionnaire indicated no clinically significant residual effects after treatment with either PMI-100 or placebo, with 2 reports of fatigue, and one report of nausea. There were no hallucinations reported as a result of treatment from either PMI-100, or placebo, and no interventions with benzodiazipines were required.

Two patients experienced moderate elevations in blood pressure within 15 minutes of treatment with PMI-100, which is consistent with known effects of ketamine. Both episodes resolved spontaneously with no sequelae. Vital signs were monitored throughout the study and there were no clinically significant changes. No abnormal laboratory values of clinical significance were reported that could not be attributed to a previous condition.

The overall safety of treatment with PMI-100 for the treatment of breakthrough pain was shown to be similar to treatment with placebo. Although patients experienced more specific side effects after treatment with PMI-100 than after placebo, these transient side effects were mild and might be considered inconveniences rather than obstacles to ketamine treatment.

Discussion and Overall Conclusions

During this 2 site, 2 phase crossover study, patients used an Numeric Pain Intensity Scale to rate their response to self-administered intranasal ketamine hydrochloride (PMI-100) or placebo for the relief of pain of >5 in intensity in 2 separate breakthrough pain episodes. All of these patients were opioid experienced, with daily, around-the-clockopioid regimens equivalent to at least 60 mg/day morphine for the treatment of chronic pain, and additional, short-acting opioids equivalent to at least 5 mg morphine for breakthrough pain episodes. The primary endpoint of the study was to compare the average reduction in pain intensity during a breakthrough pain episode after treatment with PMI-100 compared to placebo. The results of the study indicate that 1 to 5 sprays (10 to 50 mg) of self-administered intranasal PMI-100 compared to placebo demonstrated a highly statistically significant ($p<0.0001$) reduction in average pain intensity over the 60 minute observation period. The average number of sprays administered was 4.65 for PMI-100, indicating a therapeutic effect towards the higher end of the dose range of 10 to 50 mg. All time points from 10 minutes through 60 minutes showed a statistically significant reduction in pain intensity for PMI-100 compared to placebo. The statistically significant reduction in pain intensity within 10 minutes of the initial spray of PMI-100, and 4 minutes of administration of 5 sprays of PMI-100 is clinically relevant. In addition, patients required significantly more additional rescue medication for breakthrough pain episodes treated with placebo than for episodes treated with PMI-100. Considered to be a clinically relevant reduction in pain intensity from baseline, significantly more patients achieved a 40% or greater overall reduction in pain intensity after treatment with PMI-100 compared to treatment with placebo.

Intranasal administration of PMI-100 for the treatment of breakthrough pain was well-tolerated, with no serious adverse events, deaths, treatment-related drop outs, or clinically significant side effects. The nasal spray was well tolerated with a change in taste being the most frequently reported effect after treatment with PMI-100 at a rate of 3/20 (15%) patients. A review of the literature published regarding the use of intranasal ketamine reveals little about the possibility of unpleasant dissociative side effects at sub-anesthetic dose levels of ketamine. In order to understand fully the potential for dissociative effects following intranasal treatment with PMI-100, a retrospective questionnaire was designed for this study that covered the range of psychotomimetic effects that could potentially occur. As with most solicitation tools, the prevalence of reported effects becomes somewhat inflated when providing a "menu" of items to choose from. The results of the side effect questionnaire indicate that the majority of effects were mild and transient, and few patients experienced troublesome disorientation or feelings of unreality, and no patients experienced hallucination or required intervention with benzodiazipines. Given the overall unpleasantness of an intense episode of breakthrough pain despite the use of around-the-clock opioids, the transient effects of ketamine appear to be of no consequence in light of the pain-relieving qualities experienced after treatment during this study.

In conclusion, this randomized, placebo-controlled, double blind, pilot study in 20 patients has demonstrated that intranasal ketamine is a highly efficacious treatment for malignant and non-malignant breakthrough pain and shows a large margin of safety in patients on chronic opioid therapy. The profile of this experimental treatment as demonstrated from this study is one of rapid onset, transnasal absorption, possible titrateability, ease of use, and acceptance by patients and for these reasons makes it ideally suited for the treatment of breakthrough pain.

EXAMPLE 2

An Acute Subcutaneous Neurotoxicity Study in Rats with PMI-100

This Example evaluates the neurotoxicity of a formulation of ketamine hydrochloride (referred to hereafter as "PMI-100") in rats following a single subcutaneous injection. PMI-100 is a formulation containing 100 mg ketamine/ml and 0.002% benzalkonium chloride. The findings are based on the level of neuronal vacuolation.

Materials and Methods

This study included 160 rats with 16 male and 16 female rats in each of the following five treatment groups: Group 1 was given sterile water for injection (control); Group 2 was given 4 mg/kg PMI-100; Group 3 was given 15 mg/kg PMI-100; Group 4 was given 60 mg/kg PMI-100; and Group 5 was given 0.5 mg/kg MK-801. Four rats of each sex in each of these five groups were allocated to four study subgroups (Subgroups A, B, C, and D). The rats in Subgroup A were necropsied approximately six hours post-dose. Those in Subgroup B were necropsied approximately 24 hours post-dose. The rats in Subgroup C were necropsied approximately 72 hours post-dose, and those in Subgroup D were necropsied 14 days post-dose. Tabel A illustrates the specific criteria of each group and subgroup. Table B illustrates the details of the subgroups and the stains employed for evaluating the brain sections.

TABLE A

Experimental Study Design - Acute Neurotoxicity Study

| Group | No. of Animals | | Dose Material | Approximate Dose Level (mg/kg) | Dose Conc. (mg/mL) | Dose Volume (µL/kg) |
|---|---|---|---|---|---|---|
| | Male | Female | | | | |
| 1 | 16 | 16 | Vehicle | 0 | 0 | 600 |
| 2 | 16 | 16 | PMI-100 | 4 | 100 | 50 |
| 3 | 16 | 16 | PMI-100 | 15 | 100 | 150 |
| 4 | 16 | 16 | PMI-100 | 60 | 100 | 600 |
| 5 | 16 | 16 | MK-801 | 0.5 | 5 | 100 |

TABLE B

Subgroup Information - Acute Neurotoxicity Study

| Designation | Study Purpose |
|---|---|
| Subgroup A | Animals euthanized at ~6 hours post-dose (day 0) primarily for evaluation of neuronal vacuolation (H&E staining) |
| Subgroup B | Animals euthanized at ~24 hours post-dose (day 1) primarily for evaluation of neuronal vacuolation (H&E staining) and neuronal necrosis (Fluro-jade/DAPI staining). |
| Subgroup C | Animals euthanized at ~72 hours post-dose (day 3) primarily for evaluation of neuronal necrosis (Cupric Silver staining). |
| Subgroup D | Functional Observation Battery, ("FOB") and learning/memory evaluations conducted on this Subgroup. Animals euthanized at 14 days post-dose (day 14) primarily for evaluation of neuronal necrosis (Cupric Silver staining). |

Histotechnology Procedures.

Prior to necropsy, the rats were anesthetized and then subjected to intracardiac perfusion for optimal fixation. The brains of rats in Subgroups C and D were removed and imbedded in a gelatin matrix (16 brains in each block), frozen, serially sectioned at 40 micrometers. Representative step sections (between 33 and 34 for each rat) were stained with a cupric silver stain according to the method of de Olmos, which is incorporated herein by reference (Fix et al., Toxicol. Pathol. 1996, 24:291-304; Switzer, R. C., New York Acad. Sci. 1993, 679:341-348; Switzer, R. C., Toxicol. Pathol. 2000, 28:70-83). Of the 33-34 sections present for each rat brain, approximately 17 included the posterior cingulate and retrosplenial cortices.

The brains from the rats in Subgroups A and B were completely sliced in a standardized fashion to yield nine coronal sections, with each coronal slice being between 2-3 millimeters in thickness. Of these nine coronal sections, one included the posterior cingulate cortex, while three passed through the retrosplenial cortex. Two sagittal sections of the olfactory bulbs were also prepared. The coronal brain slices were placed anterior face down (the olfactory bulbs medical surface down) within tissue cassettes, processed to paraffin with a Citadel® tissue processor (Shandon Lipshaw), and embedded in paraffin following standardized procedures. The paraffin blocks were sectioned at a thickness of approximately 5 micrometers using a rotary microtome. All brain sections from the rats in Subgroups A and B were stained with hematoxylin and eosin (H&E). In addition, duplicate sections of brain from the rats in Subgroup B were also stained with Fluoro-Jade B, using DAPI (4', 6-diamidino-2-phenylindole) as a counterstain. The Fluoro-Jade B procedure has been described previously in Schmued, L C and Hopkins, K J., Brain Research 2000, 874:123-130 and in Schmued, L C and Hopkins, K J., Toxicologic Pathology 2000, 28:91-99, which are both incorporated herein by reference.

The cupric silver technique is the most sensitive stain for demonstrating degenerative neurons (i.e., of the three stains used in this study). The H&E stain is the least sensitive (or least specific) stain, with the sensitivity of the Fluoro-Jade B stain lying in between that of the H&E and cupric silver stain. However, the cupric silver stain is frequently also characterized by non-specific staining that may be confused with bone fide neuoronal degeneration. In this study, for example, the lateral hypothalamic area frequently contained well-stained fragmented axons that were present with equal frequency in the control and treated rats. This staining pattern was interpreted as being artifactual in nature and, therefore, was not documented. Similarly, small numbers of axons with a fragmented or "beaded" appearance were frequently found in other regions of the brain. These were not documented unless two or more stained axons were present in relatively close proximity (e.g. within one medium power field). The presence of two or three such stained axons would have received a grade of "minimal" for axonal degeneration. However, in the case of degenerating neurons, even one darkly-stained shrunken neuron would have received a minimal grade for neuronal degeneration. (Note the "neuron degeneration" rather than "neuron necrosis" was used for the cupric silver-stained sections, because it was often not possible to definitively identify a necrotic phenotype with this stain.) Darkly-stained neurons without a necrotic phenotype (e.g. with well preserved nuclear detail) were considered to represent artifactual "dark neurons" and were not documented. Darkly-stained (presumably degenerative) astrocytes within cupric silver-stained sections were also not documented, these cells being present in approximately equal numbers within both control and treated rat brains.

Dark granular staining of scattered glomeruli within the olfactory bulbs of rats is quite common in sections stained with the cupric silver technique and is considered to represent normal background degeneration/remodeling. Although a greater frequency of this staining is evident within treated rats in Subgroup C versus controls, this is not considered to be of biologic significance based on past experience with this stain and this particular staining pattern. Because numerous other studies that have been evaluated have shown mild to moderate degrees of olfactory glomerular degeneration within 100% of control animals, the inter-group differences in this particular study are thought to be the result of two factors: (1) that the control and treated rat brains were embedded in different blocks (i.e., with all 16 control group brains in Subgroups C and D having been blocked, together); and (2) the fact that the degree of this staining varies considerably from section to section.

Minimal degrees of axonal degeneration within cupric silver-stained sections (i.e., usually two or three axons within one intermediate power field) or of neuron degeneration (usually one neuron within one intermediate power field) can be overlooked as representing background change. Therefore, only neuron degeneration graded as being mild or greater in degree within cupric silver-stained sections was considered to be of biologic significance. Such degrees of degeneration were present only in the MK-801-treated rats.

Microscopic Evaluations.

All slides were examined in "blinded" fashion (i.e., without knowledge of treatment group assignment). The labels present on the microscope slides for Subgroups A and B included the treatment group designation and were, therefore, covered with opaque tape and the animal identifications replaced with letter codes. No labels were present on the cupric silver-stained slides, with only a key being present inside the slide box cover to indicate the animal number for each of the sixteen sections present on each slide. Microscopic findings were hand-recorded by the pathologist onto individual animal work sheets, with one sheet/animal being present for each set of H&E, Fluoro-Jade B, and cupric silver-stained slides. Diagnoses were either hand-written or numbers were used to indicate diagnoses present within a standard list (list included with raw data). All observations were also given one of five grades of severity (minimal, mild, moderate, marked, or severe). Distribution patterns of focal, multifocal, or diffuse were also assigned to any microscopic observations.

After removing the tape to "unblind" the animal numbers and group assignments, the hand-recorded data were entered into a PC-based computer program (GLPATH available from Great Laboratory Programs®). The computer protocol for this study was set up to include only 31 representative neuroanatomic regions, these having been selected based both on the potential for lesions to develop in these regions and to indicate the levels of brain that were examined. However, all areas/structures within every section were examined, not just the posterior cingulate and retrosplenial cortices.

All 33-34 cupric silver-stained sections per rat (Subgroups C and D) were also examined microscopically.

Results and Discussion

The microscopic findings for this study are discussed by subgroup.

Subgroup A.

The rats in Subgroup A had been euthanized approximately six hours post-injection. Only H&E-stained brain sections were examined from these rats, primarily to look for evidence of neuron cytoplasmic vacuolation (especially within the posterior cingulate and retrosplenial cortices) typical of that seen following treatment with NMDA receptor antagonists such as MK-801 (Fix et al., Toxicol. Pathol. 1996, 24:291-304; Fix et al., Experimental Neurology 1993, 123:204-215). This typical pattern of neuron vacuolation within the retrosplenial cortex, primarily involving neurons within Layers 2 and 3 of the cortex, was limited to the MK-801-treated rats in this study and was most prominent in the female rats. Only one male rat treated with MK-801 had such vacuolation, and this vacuolation was only minimal in degree. While this same male rat (#4876) also had a minimal degree of neuron necrosis within the retrosplenial cortex, it is not certain that this neuron necrosis was the result of the MK-801.

In contrast to the male rats, all four of the Subgroup A female rats treated with MK-801 had mild to moderate degrees of neuronal cytoplasmic vacuolation within the retrosplenial cortex. In addition, two MK-801-treated female rats had minimal to mild degrees of vacuolation within the piriform cortex. While none of the PMI-100-treated rats had evidence of neuronal cytoplasmic vacuolation within any brain section, all four of the high dose group (60 mg/kg) PMI-100-treated rats had minimal to mild degrees of vacuolation within the molecular layer (Layer 1) of the retrosplenial cortex. This vacuolation may indicate the presence of swollen apical dendrites (i.e., from neurons present deeper within the retrosplenial cortex) or swollen axonal terminals belonging to neurons projecting to this region. However, there was no evidence at later stages of any associated neuron degeneration (see discussion for Subgroups B-D, below). Also, a similar pattern of molecular layer vacuolation was not present within any of the rats injected with MK-801.

In all of the Subgroups, there were minimal degrees of axonal degeneration within the trapezoid body of the brainstem. However, this represents a common background lesion in rats and was found in equal degrees in Control group rats and was not treatment-related.

Subgroup B.

The rats in Subgroup B had been euthanized approximately 24 hours after receiving their single injections. Both H&E and Fluoro-Jade B-stained brain sections were examined from these rats, primarily to detect any residual vacuolation and/or early evidence of neuronal necrosis within the posterior cingulate and retrosplenial cortices. In Subgroup B, one male and several female MK-801-treated rats had minimal to mild degrees of neuron necrosis within the piriform cortex that were detected primarily within the Fluoro-Jade B-stained sections. None of the male rats in Subgroup B (i.e., even those treated with MK-801) had evidence of treatment-related neuron degeneration or necrosis. However, three of the four female rats treated with MK-801had minimal to mild degrees of neuron necrosis within the retrosplenial cortex. The fourth female rat treated with MK-801 was classified as having minimal "neuron, degeneration" (rather than necrosis) within its retrosplenial cortex, because it was not certain whether the microscopic changes represented basophilic neuron artifact or neuron necrosis (e.g. see Garman, R. H., Toxicol. Pathol.1990, 18:149-153.). No rats in Subgroup B that had been injected with PMI-100 had any microscopic evidence of neuron necrosis within any section of brain.

One male control group rat in Subgroup B had evidence of unilateral optic tract degeneration that involved the optic nerve, optic tract, and superior colliculus. This is a common sporadic lesion of rats that is usually unilateral but occasionally bilateral in distribution (Shibuya et al. J Vet Med Sci 1993, 55:905-912.). This lesion was also detected in rats from Subgroups C and D and is not treatment related in this study. As in Subgroup A, numerous rats in Subgroup B had evidence of minimal to mild axonal degeneration within the trapezoid body, but this was also not a treatment-related finding in this study.

Subgroup C.

The rats in Subgroup C had been euthanized approximately 72 hours after receiving their injections, with the brains from these rats having been step-sectioned and stained by the cupric silver technique to detect the presence of neuronal degeneration within the posterior cingulate and retrosplenial cortices, as well as elsewhere within the brain. There were between 33 and 34 sections from each brain.

One MK-801-treated male rat had mild neuron degeneration within the frontal cortex. Two male MK-801-treated rats had mild to moderate degrees of neuron degeneration within the retrosplenial cortex.

Mild to marked degrees of neuron degeneration within female rats were also limited to the rats in the MK-801-treatment group, with no PMI-100-treated rats having similar evidence of neuron degeneration. In the female rats treated with MK-801, such neuron degeneration was present in the piriform cortex and retrosplenial cortex. Two female rats treated with MK-801 also had evidence of mild terminal degeneration within the stratum lacunosum moleculare of the hippocampus. Such terminal degeneration within the hippocampus was not seen in PMI110-treated rats.

One control group male rat in Subgroup C had marked unilateral axonal degeneration within the optic nerve and optic tract indicative of unilateral optic tract degeneration. A similar case of spontaneous optic tract degeneration was present in one female rat in Group 2 (4 mg/kg PMI-100).

Subgroup D.

The rats in Subgroup D had been euthanized 14 days after receiving their injections, with the brains from these rats being step-sectioned and stained by the cupric silver technique to detect the presence later stages of neuronal necrosis within the posterior cingulate and retrosplenial cortices (as well as elsewhere within the brain). As in Subgroup C, the female rats treated with MK-801 were most prominently affected. (Note that, as with Subgroup C, olfactory bulb glomerular degeneration and minimal degrees of neuron degeneration are not considered to be of any biologic significance.) Mild neuron degeneration was found within the retrosplenial cortex of one MK-801-treated male rat. Neuron degeneration graded as being either "mild" or "moderate" was found in the retrosplenial cortex of all four of the MK-801-treated female rats in Subgroup D. However, as in the other subgroups on this study, no such degeneration was found within any of the brain sections from rats treated with the PMI-100. All four of the MK-801-treated female rats in Subgroup D also had mild synaptic terminal degeneration within the stratum lacunosum moleculare of the hippocampus. However, such degeneration was not found within any brain sections from PMI-100-treated rats.

The brain sections from one male rat in Group 2 (4 mg/kg PMI-100) were characterized by spontaneous optic tract degeneration, a condition already discussed as representing a spontaneous "background lesion."

Conclusions

Blinded microscopic evaluations were performed on brain sections from rats given one subcutaneous injection of either sterile water, MK-801 or the PMI-100 formulation of ketamine hydrochloride. Sections of the brains were examined from 4 female and 4 male rats at each of 6 hours, 24 hours, 72 hours, and 14 days post-injection, with these sections having been stained with either H&E, Fluoro-Jade B, or the cupric silver technique. Neuron vacuolation and degeneration within the retrosplenial cortex of the type typically seen with NMDA receptor antagonists was limited to the rats injected with MK-801 and was most prominent in the female rats. Although these alterations were not present in the rats injected with any of the three dosages of PMI-100 used in this study (viz. 4, 15, or 60 mg/kg), the female rats in the high dose PMI-100 group did have minimal to mild degrees of vacuolation within the molecular layer (Layer 1) of the retrosplenial cortex at 6 hours (within the H&E-stained sections). However, no evidence of neuron degeneration was seen in the females from this dose group at later time points (within sections stained either with H&E, Fluoro-Jade B, or the cupric silver technique). It is likely that the molecular layer vacuolation may represent transient swelling within dendritic or axonal terminals.

This study had no-observable-effect level for the PMI-100 formulation of ketamine hydrochloride in this particular study of 60 mg/kg for the male rats and 15 mg/kg for the female rats. The ketamine hydrochloride formulation containing benzalkonium chloride also did not produce any permanent degenerative alterations.

EXAMPLE 3

A 28-Day Subcutaneous Neurotoxicity Study in Rats in PMI-100

The objective of this study was to evaluate the potential neurotoxicity of the test article in the rat following multiple subcutaneous injections of the PMI-100 formulation containing 10 mg/kg (10% w/v) ketamine hydrochloride and 0.002% benzalkonium chloride solution. The formulation was given once daily over a 28-day period.

Methods 192 rats were distributed across five treatment groups as indicated in Table A. Summary information, including dosing information and the stains employed for evaluating the brain sections, are presented in Text Tables A and B, below.

TABLE A

Experimental Study Design - Acute Neurotoxicity Study

| Group | No. of Animals | | Dose Material | Approximate Dose Level (mg/kg) | Dose Conc. (mg/mL) | Dose Volume (µL/kg) |
|---|---|---|---|---|---|---|
| | Male | Female | | | | |
| 1 | 20 | 20 | Vehicle | 0 | 0 | 600 |
| 2 | 20 | 20 | PMI-100 | 4 | 100 | 40 |
| 3 | 20 | 20 | PMI-100 | 15 | 100 | 150 |
| 4 | 20 | 20 | PMI-l00 | 60 | 100 | 600 |
| 5 | 16 | 16 | MK-801 | 0.3-0.5 | 3-5 | 100 |

TABLE B

Subgroup Information - Acute Neurotoxicity Study

| Subgroup Designation | Study Purpose |
|---|---|
| Subgroup A | Animals euthanized at ~6 hours post-dose (day 27) primarily for evaluation of neuronal vacuolation (H&E staining). |
| Subgroup B | Animals euthanized at ~24 hours post-dose (day 28) primarily for evaluation of neuronal vacuolation (H&E staining) and neuronal necrosis (Fluro-Jade/DAPI staining). |
| Subgroup C | Animals euthanized at ~72 hours post-dose (day 30) primarily for evaluation of neuronal necrosis (Cupric Silver staining). |
| Subgroup D | Functional Observation Battery ("FOB") and learning/memory evaluations conducted on this Subgroup. Animals euthanized at 14 days post-dose (day 41) primarily for evaluation of neuronal necrosis (Cupric Silver staining). |

Histotechnology Procedures.

Prior to necropsy, the rats had been anesthetized and then subjected to intracardiac perfusion for optimal fixation. The heads from the rats in Subgroups C and D had been sent to NeuroScience Associates in Knoxville, Tenn. where the brains had been removed and multiply imbedded in a gelatin matrix (with 16 brains in each block), frozen, serially sectioned at approximately 40 micrometers (through the cerebral hemispheres but not into the cerebellum), and representative step sections (between 33 and 34 for each rat) stained with the amino cupric silver stain according to the method of de Olmos et al. (1994; Fix, 1996; Switzer, 1993, 2000).

Of the 33-34 sections present for each rat brain, approximately 17 included the posterior cingulate and retrosplenial cortices.

The brains from the rats in Subgroups A and B were sent to Consultants In Veterinary Pathology, Inc. where the brains were completely sliced in a standardized fashion to yield nine coronal sections, with each coronal slice being between two and three millimeters in thickness. Of these nine coronal sections, one included the posterior cingulate cortex, while three passed through the retrosplenial cortex. Two sagittal sections of the olfactory bulbs were also prepared. The coronal brain slices were placed anterior face down (the olfactory bulbs medial surface down) within tissue cassettes, processed to paraffin with a Citadel® tissue processor (Shandon Lipshaw), and embedded in paraffin following standardized procedures. The paraffin blocks were sectioned at a thickness of approximately 5 micrometers using a rotary microtome. All brain sections from the rats in Subgroups A and B were stained with hematoxylin and eosin (H&E). In addition, duplicate sections of the brains from rats in Subgroup B were also stained with Fluoro-Jade B, using DAPI (4', 6-Diamidino-2-Phenylindole) as a counterstain. The Fluoro-Jade B procedure that was used is that reported by Schmued et al (2000). (Schmued, L. C., Hopkins, K J (2000) Brain Res. 874:123-130. Fluoro-Jade B: a high affinity fluorescent markers for the localization of neuronal degeneration.; Schmued, L. C., Hopkins, K. J. (2000) Toxicol. Pathol. 28: 91-99. Fluoro-Jade: Novel fluorochromes for detecting toxicant-induced neuronal degeneration.

Microscopic Evaluations.

All slides were examined in "blinded" fashion. Once "unblinded" the animal identifications were entered into a PC-based computer program (GLPATH; Great Laboratory ProgramS). The computer protocol for this study was set up to include between 25 (for the cupric silver-stained sections) and 31 (for the H&E and Fluoro-Jade B-stained sections) representative neuroanatomic regions, these having been selected based both on the potential for lesions to develop in these regions and to indicate the levels of brain that were examined. All 30-34 cupric silver-stained sections/rat were also examined microscopically. For the Subgroup B rats, slightly different diagnoses were used for findings made on H&E-stained sections and on those stained with Fluoro-Jade B. For example the term "neuron necrosis" indicates the presence of "red dead neurons" as seen with H&E. However, neuron necrosis within a Fluoro-Jade B-stained section would have received a diagnosis of "Fluoro-Jade Staining."

Results

Subgroup A.

The rats in Subgroup A had been euthanized approximately six hours after their final subcutaneous injections. Only H&E-stained brain sections were examined for evidence of neuron cytoplasmic vacuolation typical of that seen following treatment with NMDA receptor antagonists such as MK-801 (Fix et al., 1993, 1996) (Fix, A. S., Horn, J. W., Lightman, K. A., Johnson, C. A., Long, G. G., Storts, R. W., Farber, N. Wozniak, O. F., Olneg, J. W. (1993), Exp. Neruol. 123: 204-215. Neuronal vacuolization and necrosis induced y the non-competitive N-methyl-D-aspartate (NMDA antagonist MK(+)801, (dizocilpine maleate), a light and electron microscopic evaluation of the rat retrosplineal cortex.; Fix, A. S., Ross, J. F, Stitzer, S. R. Switzer, R. C. (1996) Toxicol Pathol. 24: 291-304. Integrated evaluation of the central nervous system lesions: stains for neurons, astrocytes, and microglia reveal the spatial an temporal features of MK-801 induced neuronal necrosis in the rat cerebral cortex.)

This pattern of neuron vacuolation (which typically involves neurons within Layers II and III of the retrosplenial cortex) was not found within any of the rats in this phase of the study. For the females in Subgroup B, one rat in each of Groups 1 and 2 plus two rats in Group 5 (i.e. MK-801-treated) had minimal neuron necrosis considered to be within background frequency and to be of no biologic significance.

Subgroup B.

The rats in Subgroup B had been euthanized approximately 24 hours after the final injection. Both H&E and Fluoro-Jade B-stained brain sections were examined from these rats to detect any residual vacuolation and/or early evidence of neuronal necrosis within the posterior cingulate and retrosplenial cortices. In the male rats, minimal Fluoro-Jade staining was present within the piriform cortex of one rat and in the tenia tecta of another rat. However, such minimal Fluoro-Jade staining is within the expected background frequency.

In the female rats, both minimal to mild neuron necrosis (on H&E) and minimal to mild Fluoro-Jade staining were present within the retrosplenial cortex of either two or three rats in the MK-801-treated group (Group 5). However, no such alterations were seen in rats injected with PMI-100.

Subgroup C.

The rats in Subgroup C had been euthanized approximately 72 hours after receiving their final injections. The brains from these rats had been step-sectioned and stained by the amino cupric silver technique to detect the presence of neuronal degeneration within the posterior cingulated and retrosplenial cortices, as well as elsewhere within the brain.

Mild to moderate degrees of neuron degeneration were limited, in Subgroup C, to rats injected with MK-801 and were found most frequently within the retrosplenial cortex. The degree of MK-801-associated neuron degeneration was greatest in the female rats. Mild neuron degeneration was also found within the piriform cortex of two MK-801-treated female rats, as was synaptic terminal degeneration within the stratum lacunosum moleculare of the hippocampus. This latter pattern of degeneration was seen in three of four Subgroup C female rats present in treatment Group 5.

Subgroup D.

The rats in Subgroup D had been euthanized 14 days after receiving their final injections, with the brains from these rats being step-sectioned and stained by the cupric silver technique to detect the presence later stages of neuronal necrosis within the posterior cingulate and retrosplenial cortices. No male rats in Subgroup D had any treatment-related histologic alterations, although there were sporadic findings of minimal degrees of neuron degeneration (i.e. only one or two neurons) in a variety of locations but without any evidence of a dose effect. In the female rats in Subgroup D, treatment-related lesions were confined to the retrosplenial cortex of MK-801-treated rats. All four of the female rats treated with MK-801 had mild to moderate degrees of axon degeneration within the retrosplenial cortex. While two females in Group 2 had foci of minimal axon degeneration within the retrosplenial cortex, this alteration was confined to one section level, only, and probably represented artifact. For the MK-801-treated females, on the other hand, the axonal staining and fragmentation was present within multiple sections throughout much of the retrosplenial cortex.

The fact that female rats in Subgroup C that were treated with MK-801 had neuronal degeneration within the retrosplenial cortex but that MK-801-treated females in Subgroup D only had axonal degeneration in this region suggests that the somas of the necrotic neurons had disappeared over the intervening 11 day period.

Discussion

In conclusion, there is no evidence that treatment of rats with PMI-100 formulations of ketamine hydrochloride and benzalkonium chloride, under the conditions of this subacute study, resulted in any neuropathologic alterations. The only treatment-related lesions were in the rats treated with MK-801, with these being the classical late-stage lesions of neuron and axon degeneration within the retrosplenial cortex. Retrosplenial cortex neurons with vacuolated cytoplasm were not found within this subacute phase of the study. Neither was there any evidence of the pattern of minimal to mild vacuolation noted in Layer I of the Group 4 females necropsied six hours after receiving a single subcutaneous dose of PMI-100 (in the previously performed acute study). Finally, no inter-group differences in overall cellularity of the retrosplenial cortices were noted.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, publications, product descriptions, and protocols are cited throughout this application, the disclosures of which are incorporated by reference herein in their entireties for all purposes.

What is claimed is:

1. A pharmaceutical composition which comprises an aqueous solution containing about 10% ketamine hydrochloride and about 0.002% benzalkonium chloride, wherein the composition does not cause any significant neurotoxicity, and wherein the level of neurotoxicity is comparable to sterile water when administered.

2. The pharmaceutical composition of claim 1, further comprising a suitable carrier selected from the group consisting of water, saline, bicarbonate, sucrose and mixtures thereof.

3. A pharmaceutical composition which comprises an aqueous solution containing about 10% ketamine hydrochloride and about 0.001% to about 0.2% benzalkonium chloride, wherein the composition does not cause any significant neurotoxicity, and wherein the level of neurotoxicity is comparable to sterile water when administered.

4. A pharmaceutical composition which comprises an aqueous solution containing about 0.01 mg/kg to about 1 mg/kg ketamine hydrochloride and about 0.00 1% to about 0.2% per unit dose benzalkonium chloride, wherein the composition does not cause any significant neurotoxicity, and wherein the level of neurotoxicity is comparable to sterile water when administered.

* * * * *

UNITED STATES PATENT AND TRADEMARK OFFICE
CERTIFICATE OF CORRECTION

PATENT NO.        : 7,273,889 B2                                              Page 1 of 1
APPLICATION NO.   : 10/256283
DATED             : September 25, 2007
INVENTOR(S)       : Mermelstein et al.

It is certified that error appears in the above-identified patent and that said Letters Patent is hereby corrected as shown below:

On the Title page, Item 45 and Item
[*] Notice:    Subject to any disclaimer, the term of this patent is extended or adjusted under 35 USC 154(b) by (250) days Delete the phrase "by 250" and insert -- by 288 days--

Signed and Sealed this

Sixth Day of November, 2007

JON W. DUDAS
*Director of the United States Patent and Trademark Office*